(12) United States Patent
Boonstra et al.

(10) Patent No.: US 9,080,133 B2
(45) Date of Patent: Jul. 14, 2015

(54) GLUTAMIC ACID N,N-DIACETIC AMIDE, GLUTAMIC ACID N-ACETIC AMIDE N-ACETONITRILE, ALKALI METAL SALTS THEREOF, PROCESS TO PREPARE THEM AND THEIR USE

(75) Inventors: Tjerk Oedse Boonstra, Duiven (NL);
Martin Heus, Arnhem (NL); Axel Carstens, Kleve (DE); Jim Lepage, Chicago, IL (US)

(73) Assignee: AKZO NOBEL N.V., Arnhem (NL)

( * ) Notice: Subject to any disclaimer, the term of this patent is extended or adjusted under 35 U.S.C. 154(b) by 549 days.

(21) Appl. No.: 12/673,683

(22) PCT Filed: Aug. 14, 2008

(86) PCT No.: PCT/EP2008/060656
§ 371 (c)(1),
(2), (4) Date: Apr. 26, 2010

(87) PCT Pub. No.: WO2009/024519
PCT Pub. Date: Feb. 26, 2009

(65) Prior Publication Data
US 2010/0222610 A1    Sep. 2, 2010

Related U.S. Application Data

(60) Provisional application No. 60/968,432, filed on Aug. 28, 2007.

(30) Foreign Application Priority Data

Aug. 17, 2007  (EP) .................................. 07114558

(51) Int. Cl.
| C07C 229/24 | (2006.01) |
| C11D 3/33 | (2006.01) |
| C07C 227/26 | (2006.01) |
| C07C 237/06 | (2006.01) |
| C07C 255/25 | (2006.01) |
| C09K 8/86 | (2006.01) |
| C11D 7/32 | (2006.01) |
| D21C 9/10 | (2006.01) |

(52) U.S. Cl.
CPC ............... *C11D 3/33* (2013.01); *C07C 227/26* (2013.01); *C07C 229/24* (2013.01); *C07C 237/06* (2013.01); *C07C 255/25* (2013.01); *C09K 8/86* (2013.01); *C11D 7/3245* (2013.01); *D21C 9/10* (2013.01)

(58) Field of Classification Search
CPC .. C07C 229/16; C07C 237/06; C07C 227/26; C07C 229/24; C07C 255/25; C09K 8/86; C11D 7/3245
See application file for complete search history.

(56) References Cited

U.S. PATENT DOCUMENTS

2008/0300159 A1    12/2008   Seebeck et al.

FOREIGN PATENT DOCUMENTS

| EP | 0 783 034 | 7/1997 |
| EP | 0 884 381 | 12/1998 |
| EP | 1 004 571 | 5/2000 |
| EP | 1 803 801 | 7/2007 |
| JP | 11-092436 | 4/1999 |
| JP | 11-092436 A * | 4/1999 |
| JP | 2000 192091 | 7/2000 |
| JP | 2001 003089 | 1/2001 |
| JP | 2002 356464 | 12/2002 |
| WO | 96/22351 | 7/1996 |

OTHER PUBLICATIONS

International Search Report and Written Opinion, PCT International Application PCT/EP2008/60655, mailed on Jan. 13, 2009.
International Preliminary Report on Patentability, PCT International Application PCT/EP2008/60655, mailed on Feb. 24, 2010.
Jerry March, "Advanced Organic Chemistry," 1992, John Wiley & Sons, XP 002496826, p. 887-888, p. 965, paragraph 6-50, p. 966, paragraph 6-51.
International Search Report and Written Opinion, PCT International Application PCT/EP2008/60656, mailed on Dec. 19, 2008.
International Preliminary Report on Patentability, PCT International Application PCT/EP2008/60656, dated Dec. 15, 2009.

* cited by examiner

*Primary Examiner* — Paul A Zucker
(74) *Attorney, Agent, or Firm* — Sandra B. Weiss

(57) ABSTRACT

The present invention relates to glutamic acid N,N-diacetic amide, potassium or sodium glutamate N,N-diacetic amide, glutamic acid N-acetic amide N-acetonitrile, potassium or sodium glutamate N-acetic amide N-acetonitrile, to processes to prepare such compounds and the use thereof.

16 Claims, 2 Drawing Sheets

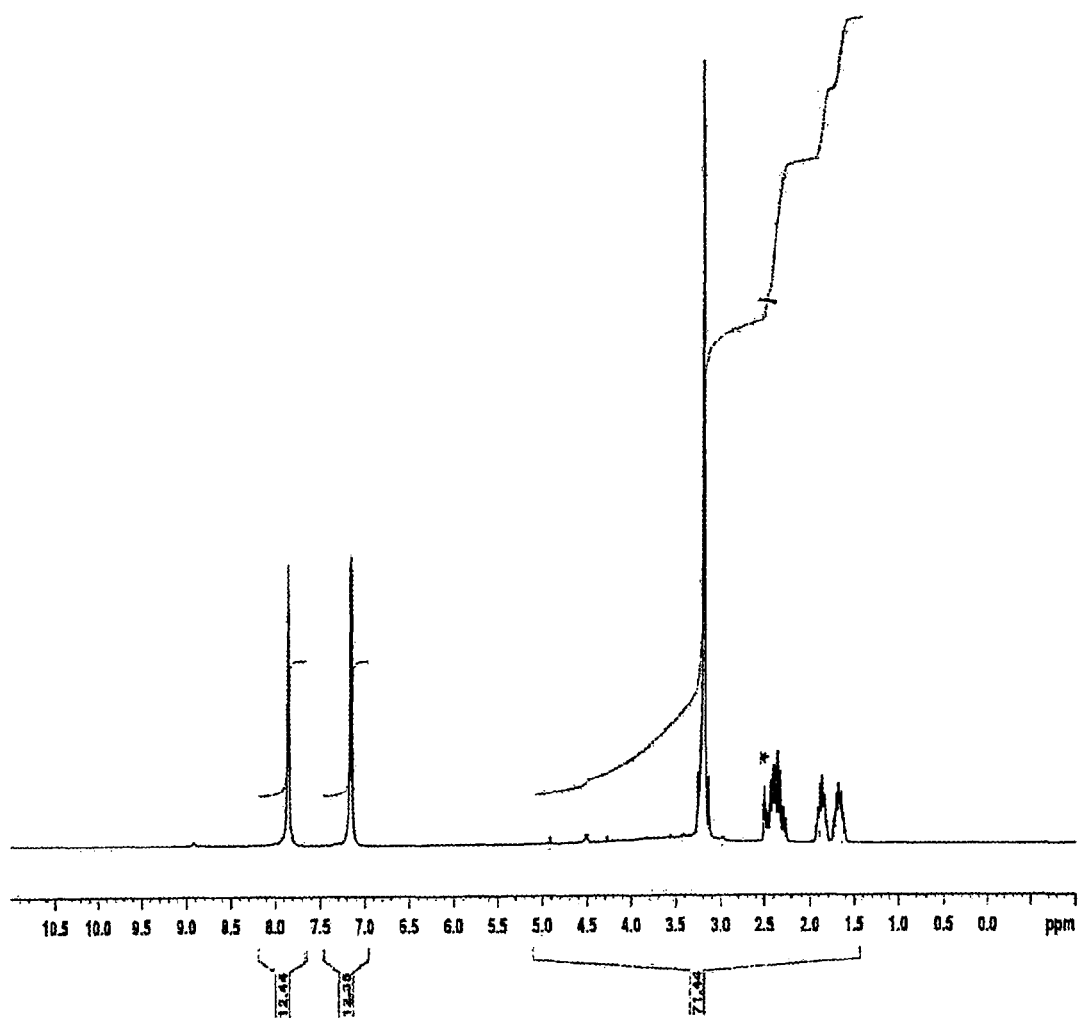

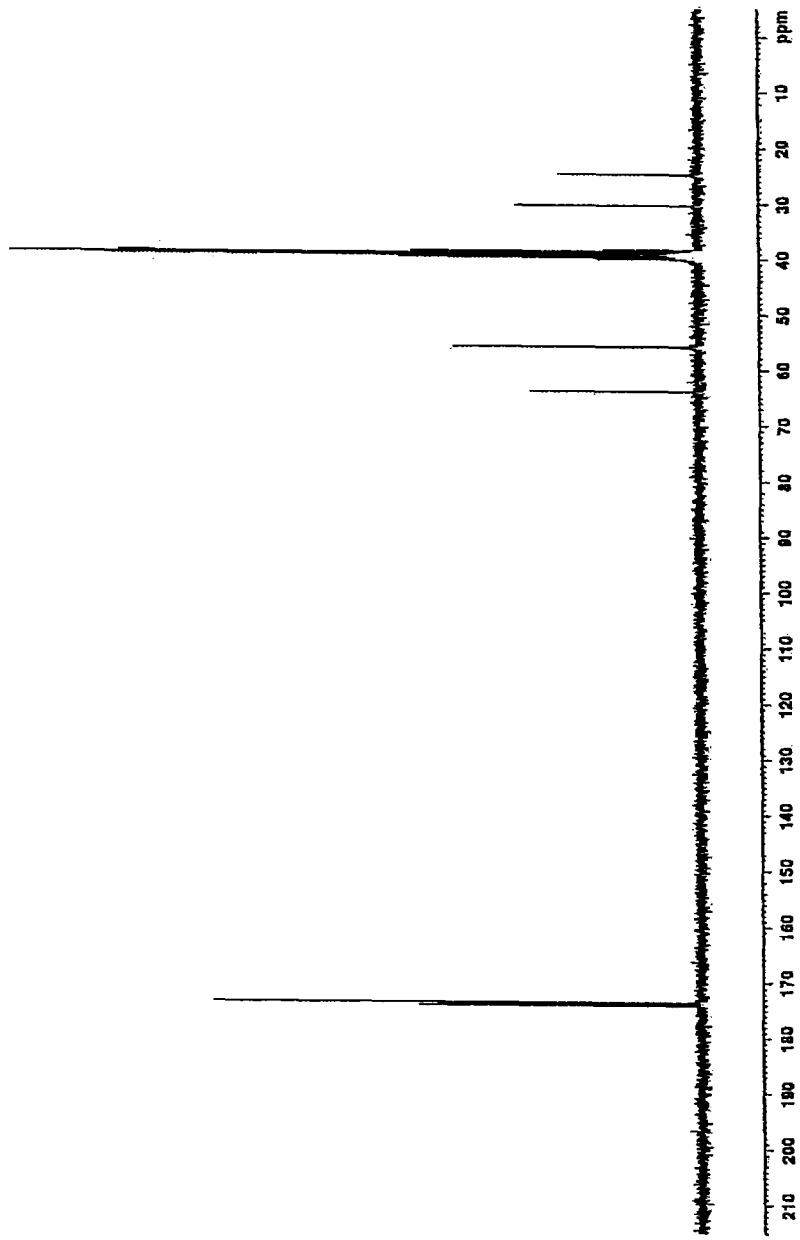

GLUTAMIC ACID N,N-DIACETIC AMIDE, GLUTAMIC ACID N-ACETIC AMIDE N-ACETONITRILE, ALKALI METAL SALTS THEREOF, PROCESS TO PREPARE THEM AND THEIR USE

REFERENCE TO RELATED APPLICATION(S)

This application is the U.S. National Phase of PCT/EP20081060656 filed on Aug. 14, 2008 and claims the benefit of U.S. Provisional Application No. 60/968,432 filed on Aug. 28, 2007.

The present invention relates to glutamic acid N,N-diacetic amide, glutamic acid N-acetic amide N-acetonitrile, alkali metal salts thereof, a process to prepare them, and their use in e.g. the preparation of pure glutamic acid N,N-diacetic acid and salts thereof.

Chelating agents are agents capable of forming a complex with a metal ion. Examples of chelating agents include compounds like EDTA (ethylenediamine N,N,N',N'-tetraacetic acid), MGDA (methylglycine N,N-diacetic acid), and GLDA (glutamic acid, N,N-diacetic acid).

GLDA is disclosed to be useful for a number of applications as it has a good biodegradability. Several documents disclose a process to prepare GLDA.

EP 884 381 in Synthesis example 1 discloses a "classic" Strecker process to prepare GLDA in the presence of a high amount of sodium hydroxide, i.e. under relatively alkaline conditions.

JP 11092 436-A in Example 3 and Example 8 discloses a process to prepare and isolate a glutamic acid N-monoacetic amide, N-monoacetic acid disodium salt. In Example 3 the starting material is glutamic acid N monoacetic acid, a raw material which is difficult to synthesize. Also, many purification steps are needed to purify the product in Example 3. In Example 8 the starting material is glutamic acid N,N-diacetonitrile, which is a much more common starting material that can be relatively easily synthesized with a Singer synthesis. However, because in this example hydrolyzing of the diacetonitrile compound takes place under alkaline conditions, the major product is the diacetic acid and only a minor amount of the monoacetic amide monoacetic acid compound is formed, as under alkaline conditions the hydrolysis will continue until there is a fully hydrolyzed carboxylic acid compound and cannot be controlled very well.

BRIEF DESCRIPTION OF THE DRAWINGS

FIG. 1 illustrates the proton-NMR of the isolated GLDamide compound of Example 1.

FIG. 2 illustrates the carbon-NMR of the isolated GLDamide compound of Example 1.

It has now surprisingly been found that if glutamic acid N,N-diacetonitrile is hydrolyzed under acidic or neutral conditions, the acetonitrile groups are converted to acetic diamide groups and not to carboxylic acid groups. It was additionally surprisingly found that the resulting glutamic acid N-acetonitrile, N-acetic amide, and glutamic acid N,N-diacetic amide can be very suitably isolated in the form of crystals.

The invention thus provides glutamic acid N,N-diacetic amide, potassium or sodium glutamate N,N-diacetic amide, glutamic acid N-acetic amide N-acetonitrile, and potassium or sodium glutamate N-acetic amide N-acetonitrile and a process to prepare them. In a specific embodiment the invention provides crystals of glutamic acid N,N-diacetic amide, potassium or sodium glutamate N,N-diacetic amide, glutamic acid N-acetic amide N-acetonitrile, and potassium or sodium glutamate N-acetic amide N-acetonitrile.

Thus, contrary to the synthesis disclosed in EP 884381, it has been found possible to prepare the acetic amides of glutamic acid in an isolatable form. Storage of GLDN for a longer period of time at a pH that is slightly acidic to neutral is found to trigger hydrolysis, but because the hydrolysis conditions are mild the hydrolysis will not be complete, resulting in the formation of an amide functionality instead of a carboxylate acid functionality.

It will be clear that these amides when precipitated and isolated can be used to synthesize highly pure GLDA solutions substantially free of by-products, by means of further hydrolysis.

Hence, in one embodiment the invention provides a process to prepare glutamic acid amides wherein hydrolysis of glutamic acid N,N-diacetonitrile, or the potassium or sodium salt thereof, takes place at a pH between 0.5 and 7 to give glutamic acid-N,N-diacetic amide, glutamic acid-N-monoacetic amide-N-monoacetonitrile or the alkali metal salt thereof, with in an optional subsequent step isolation of the glutamic acid-N,N-diacetic amide, glutamic acid N-monoacetic amide N-monoacetonitrile or the alkali metal salt thereof.

The glutamic acid amide compounds are represented by the structures: HOOC—$CH_2$—$CH_2$—CH(COOM)—N—($CH_2$—CN)($CH_2$—C(O)—$NH_2$) for the monoamide-mononitrile, or HOOC—$CH_2$—$CH_2$—CH(COOM)—N—($CH_2$—C(O)—$NH_2$)$_2$ for the diamide, wherein M=an alkali metal or H. In this application the glutamic acid amide compounds are also referred to as GLDamide.

In one embodiment the novel group of glutamic acid diacetic amide crystals is prepared by a so-called Singer route. The reaction route encompasses reacting glutamic acid with formaldehyde and hydrogen cyanide in the presence of an alkali metal hydroxide to first give glutamic acid diacetonitrile (or the monoalkali metal salt thereof). These types of products are known as aminoacetonitriles or, for short, "nitriles" and in the case of glutamic acid nitriles are also referred to as GLDN herein. GLDN is subsequently hydrolyzed to give GLDamide.

Finally, the present invention relates to the use of the amides in the preparation of glutamic acid N,N-diacetic acid or salts thereof, as a crystallization inhibitor, preferably a halite inhibitor, and in oil well applications, in a detergent composition, a descaling composition, a microbial composition, a micronutrient composition, in gas sweetening, pulp and paper bleaching, or in the preparation of any of such compositions.

In a more preferred embodiment of the process to prepare the compounds of the invention, between 1.6 and 2.4 equivalents of formaldehyde are used per equivalent of glutamic acid or salt thereof and 1.6 to 2.4 equivalents of HCN are used per equivalent of glutamic acid or salt thereof. In an even more preferred embodiment 1.9-2.1 equivalents of formaldehyde and HCN are used per equivalent of glutamic acid or salt thereof. Most preferably, the amount of formaldehyde and HCN is about 2.0 equivalents per equivalent of glutamic acid or salt thereof. In the process the amount of HCN may be (but does not need to be) the same as the amount of formaldehyde.

It will be clear that instead of starting with glutamic acid, it is possible to use sodium or potassium glutamate. The same holds for hydrogen cyanide and sodium hydroxide; sodium cyanide, potassium cyanide, and potassium hydroxide are alternatives as long as during the reaction the pH is acidic or neutral and does not become alkaline.

Preferably, the alkalimetal salts of the invention are prepared by a process comprising two or more steps, wherein in a first step a glutamic acid, a sodium or potassium salt thereof or a mixture thereof is reacted with formaldehyde and hydrogen cyanide, at a pH equal to or below 7, and in a subsequent step the nitrile compound formed in the first step is hydrolyzed.

In another embodiment the first step is split up into two substeps, firstly a reaction of glutamic acid or glutamate with formaldehyde to generate a Schiff base intermediate and subsequently a reaction with HCN and further formaldehyde to form a nitrile.

In the above preferred process the alkalimetal salts of GLDA of the present invention are prepared by a so-called Singer process. Here the process is a multi-step process (multi-step meaning two or more steps). The raw material is monosodium glutamate, glutamic acid or monopotassium glutamate. The very low solubility of glutamic acid can be overcome by dissolving it in NaOH or KOH, resulting in the formation of monosodium or monopotassium glutamate. In the manufacturing of GLDN the monosodium salt or monopotassium salt of glutamic acid is dissolved in water and formaldehyde and cyanide are added under acidic or neutral conditions. The addition of formaldehyde and hydrogen cyanide preferably takes place at a temperature between 0° C. and 40° C. The result is a product having two nitrile functionalities. The nitrile is hydrolyzed in a second step to give GLDamide.

Due to the fact that the GLDamide can be isolated as crystals and therefore can be very well stored and transported, the diacetic amide can be produced in one location and later be further hydrolyzed to the glutamic acid N,N-dicarboxylate in another location.

As starting material instead of glutamic acid also the potassium salt thereof can be employed. The main advantage of monopotassium glutamate in the production process is its very high solubility even at room temperature. Monosodium glutamic acid (MSG) has a solubility of ~40 wt % in water at room temperature, monopotassium glutamate has a solubility of ~65-70 wt % The more concentrated the glutamate can be processed, the less water removal is required to make a concentrated GLDamide solution. The monosodium GLDN (=glutamic acid amino diacetonitrile monosodium salt) manufactured has a concentration related to the maximum achievable concentration of the monosodium glutamate and the amount of water added by using aqueous formaldehyde, because water removal is not possible during the process steps. The higher the GLDamide concentration, the better the GLDamide can be isolated by precipitation/crystallization. The GLDamide precipitate can be isolated by filtration, if needed, after/while removing water.

As nitriles are relatively stable in acidic conditions, it may be advantageous to add a small amount of a well known acid like hydrochloric acid or sulfuric acid to control the pH.

In the case of the potassium version of GLDN, the final nitrile concentration can be higher due to the high solubility of potassium glutamate. It allows for more economical transport, more output per reactor volume, lower energy costs, and is an easy way to produce a high amount of GLDamide in the partial hydrolysis of the nitrile functionalities.

EXAMPLES

Example 1

Preparation of GLDamide by a Singer synthesis according to the present invention.

Preparation of GLDN

The reactor was precharged with 1,691.4 g (5 moles) of a 40% L-glutamic acid monosodium salt solution prepared from Na-glutamate monohydrate ex Fluka. 340.9 g (5 moles) of a 44% formaldehyde solution were added in 5-30 minutes. The temperature increased a little depending on the speed of dosing formaldehyde and the temperature of the formaldehyde solution (slight exotherm). The solution was cooled to room temperature. Simultaneously were dosed 270 g HCN (10 moles) and 341 g formaldehyde solution (5 moles). The temperature of the heating/cooling bath was adjusted to keep the reaction temperature below 40° C. When dosing was completed, the reaction mixture was stirred for 30-90 minutes at room temperature.

Synthesis of the GLDamide

A GLDN solution with a pH of about 4, prepared according to the above process, was heated in an oven for 3 days at 45° C. After cooling to room temperature the pH of the GLDN solution was set to about 3 by slowly adding concentrated hydrochloric acid. The clear solution was stored for more than a week at room temperature. When crystallization started, the solution was stored for 3 weeks in the refrigerator. After this the crystals were filtered, washed and dried at 40° C.-vacuum. Proton-NMR and carbon-NMR showed that the isolated compound was GLDamide. The results thereof are represented in FIGS. 1 and 2. The yield was about 35% GLDamide based on the starting amount of the nitrile.

Saponification of the GLDamide to the Sodium Salt of GLDA 1,001.3 g GLDamide (3.84 moles) were added portionwise to a mixture of 1,256.7 g 49% NaOH solution and 1,002 g water. The mixture was boiled for 2 hours at 108° C. to remove the ammonia and then cooled to room temperature. The GLDA solution was spraydried with a Niro mobile minor spray drier. The GLDA-$Na_4$ yield (determined on the basis of Fe-TSV) was about 91%.

The above demonstrates the preparation and isolation of GLDamide from a GLDN solution and the use thereof in preparing GLDA or salts thereof.

Comparative Example 2

In this Example GLDA was prepared using a "classic" Strecker synthesis as disclosed in e.g. EP 884 381.

A 3-liter double-walled reactor with a propeller-type impeller and heating bath was precharged with:
- 201.3 g monosodium glutamate (1.08 moles) ex Fluka
- 95 g 50% NaOH (1.19 moles) ex Aldrich
- 250 g water.

The mixture was heated to 92° C., and dosing was started of 499.7 g 28.3% NaCN (2.89 moles). Two minutes later, the dosing of 199.3 g 43.5% formaldehyde solution (2.89 moles) was started. Both solutions were added in a dosing time of 2 hours. At the start of the dosing the temperature of the heating bath was set to 115° C., and ammonia/water was distilled off continuously. When necessary, water was added to keep the boiling point at 110° C. When the dosing was completed, the remaining cyanide was reduced to a level<100 ppm by reacting with formaldehyde. The reaction mixture was boiled for another 100 minutes with water suppletion to keep the boiling temperature below 110° C. Then the reaction mixture was cooled to room temperature.

The resulting GLDA solution was analyzed with NMR, which showed that no GLDamide was present

The invention claimed is:

1. A solid compound of glutamic acid N,N-diacetic amide, potassium or sodium glutamate N,N-diacetic amide, glutamic acid N-acetic amide N-acetonitrile, or potassium or sodium glutamate N-acetic amide N-acetonitrile, wherein the solid compound is in isolatable form.

2. A process to prepare the acetic amide compound of claim 1, comprising the hydrolysis of glutamic acid N,N-diacetonitrile, or the potassium or sodium salt thereof, at a pH between 0.5 and 7.

3. The process of claim 2 further comprising in a subsequent step isolating the glutamic acid-N,N-diacetic amide, glutamic acid N-monoacetic amide N-monoacetonitrile or the potassium or sodium salt thereof by a crystallization or precipitation step.

4. A process to prepare the acetic amide compound of claim 1, comprising reacting glutamic acid, a sodium or potassium salt thereof or a mixture thereof with formaldehyde, hydrogen cyanide, a potassium or sodium salt thereof or a mixture thereof and potassium hydroxide, sodium hydroxide or a mixture thereof, in an aqueous solution, and in a subsequent step hydrolyzing the nitrile compound formed in the first step at a pH between 0.5 and 7.

5. The process of claim 2 further comprising performing a subsequent hydrolysis at a temperature of at least 90.degree. C. and an alkaline pH to give glutamic acid-N,N-diacetic acid or the sodium or potassium salt thereof.

6. The process of claim 4 further comprising performing a subsequent hydrolysis at a temperature of at least 90.degree. C. and an alkaline pH to give glutamic acid-N,N-diacetic acid or the sodium or potassium salt thereof.

7. A process to prepare glutamic acid N,N-diacetic acid or salts thereof comprising the step of hydrolyzing the acetic amide compound of claim 1.

8. A crystallization inhibitor comprising the solid compound of claim 1.

9. An oil well composition comprising the solid compound of claim 1.

10. A detergent composition comprising the solid compound of claim 1.

11. A descaling composition comprising the solid compound of claim 1.

12. A microbial composition comprising the solid compound of claim 1.

13. A micronutrient composition comprising the solid compound of claim 1.

14. A gas sweetening composition comprising the solid compound of claim 1.

15. A pulp and paper bleaching composition comprising the solid compound of claim 1.

16. A aqueous solution comprising glutamic acid N,N-diacetic amide, potassium or sodium glutamate N,N-diacetic amide, glutamic acid N-acetic amide N-acetonitrile, potassium or sodium glutamate N-acetic amide N-acetonitrile, wherein the solution has a pH between 0.5 and 7.

\* \* \* \* \*